United States Patent [19]

Smeltz

[11] 4,308,279

[45] Dec. 29, 1981

[54] CRYSTALLINE, INSECTICIDAL PYRETHROID

[75] Inventor: Leland A. Smeltz, Langhorne, Pa.

[73] Assignee: FMC Corporation, Philadelphia, Pa.

[21] Appl. No.: 164,125

[22] Filed: Jun. 30, 1980

Related U.S. Application Data

[63] Continuation-in-part of Ser. No. 46,147, Jun. 6, 1979.

[51] Int. Cl.³ .................... A01N 53/00; C07C 121/75
[52] U.S. Cl. ................................ 424/304; 260/465 D
[58] Field of Search ..................... 260/465 D; 424/304

[56] References Cited

U.S. PATENT DOCUMENTS

| | | | |
|---|---|---|---|
| 4,024,163 | 5/1977 | Elliott et al. | 260/347.4 |
| 4,133,826 | 1/1979 | Warnant et al. | 260/465 D |
| 4,136,195 | 1/1979 | Warnant et al. | 424/304 |
| 4,151,195 | 4/1979 | Warnant et al. | 260/465 D |
| 4,213,916 | 7/1980 | Davies et al. | 260/465 D |

FOREIGN PATENT DOCUMENTS 52-142046 11/1977 Japan.

Primary Examiner—Dolph H. Torrence
Attorney, Agent, or Firm—Robert L. Andersen; H. Robinson Ertelt; Robert M. Kennedy

[57] ABSTRACT

A crystalline, optically inactive compound, each crystal comprising an equimolar mixture of the isomers (S)-(cyano)(3-phenoxyphenyl)methyl (1R,cis)-3-(2,2-dichloroethenyl)-2,2-dimethylcyclopropanecarboxylate and (R)-(cyano)-(3-phenoxyphenyl)methyl (1S,cis)-3-(2,2-dichloroethenyl)-2,2-dimethylcyclopropanecarboxylate, its preparation by a cyclic crystallization/equilibration process, and its utility as an insecticide are described and exemplified.

4 Claims, No Drawings

CRYSTALLINE, INSECTICIDAL PYRETHROID

This application is a continuation-in-part of copending application Ser. No. 046,147 filed June 6, 1979.

The present invention relates to an insecticidal pyrethroid and a method for preparation. More particularly the invention relates to the pyrethroid (cyano)(3-phenoxyphenyl)methyl- 3-(2,2-dichloroethenyl)-2,2-dimethylcyclopropanecarboxylate. In accordance with one aspect of the present invention there is provided a crystalline, insecticidal compound in which each crystal contains substantially equimolar amounts of (s)-cyano)-(3-phenoxyphenyl)methyl (1R,cis)-3-(2,2-dichloroethenyl)-2,2-dimethylcyclopropanecarboxylate (1R,cis-α-S isomer) and its enantiomer, (R)-(cyano)(3-phenoxyphenyl)methyl (1S,cis)-3-(2,2-dichloroethenyl)-2,2-dimethylcyclopropanecarboxylate (1S,cis-α-R isomer). In accordance with a second aspect of the invention there is provided an improved cyclic process for producing the claimed compound.

U.S. Pat. No. 4,024,163 describes dihalovinylcyclopropanecarboxylates in general, including dibromo- and dichlorovinylcyclopropanecarboxylates, but not the novel compound of this invention. That patent discloses separation of a single optically active isomer, (S)-(cyano)(3-phenoxyphenyl)methyl (1R,cis)-3-(2,2-dibromovinyl)-2,2-dimethylcyclopropanecarboxylate from its 1R,cis-α-R diasterometer, by crystallizing a mixture of these two diastereomers from hexane. U.S. Pat. No. 4,133,826 discloses a comparable crystallization technique utilizing these isomers of the dibromo or dichloro compound, using isopropanol as a solvent.

U.S. Pat. No. 4,136,195 discloses the 1R,cis-α-S and 1R,cis-α-R isomers and mixtures of these two diastereomers of α-cyano-3-phenoxybenzyl 2,2-dimethyl-3R-(2,2-dichlorovinyl)cyclopropane-1R-carboxylate, but does not disclose the claimed compound. This patent also teaches the 1R,cis-α-S isomer is the more active of the disclosed diastereomers, and that the 1R,cis-α-R and 1R,cis-α-S isomers may be separated chromatographically.

Japanese Kokai No. 52-142046 discloses the four isomers of the dl-trans and of the dl-cis forms of α-cyano-3-phenoxybenzyl 2,2-dimethyl-3-(2,2-dichlorovinyl)cyclopropanecarboxylate, the relationship of the four isomers in each group to each other, and the chromatographic separation of a crystalline pair of cis isomers which is described as containing the "ineffective substances" (Relative effectiveness=3) from an oily mixture of cis isomers, described as the "effective substances" (Relative effectiveness=189).

U.S. Pat. Nos. 4,151,195 and 4,136,195 disclose equilibration between the 1R,cis-α-R and 1R,cis-α-S diastereomers of (cyano)(3-phenoxyphenyl)methyl 3-(2,2-dichlorovinyl)-2,2-dimethylcyclopropanecarboxylate by reacting the 1R,cis-α-R or 1R,cis-α-S diastereomer or a non-equimolar mixture thereof with a base in the presence of a solvent, and then recovering (a) the 1R,cis-α-S diastereomer as a crystalline solid (m.p. 55°-57° C.) (4,136,195) or (b) the equilibrated diastereomeric mixture of 1R,cis-α-R and 1R,cis-α-S isomers (U.S. Pat. No. 4,151,195).

The racemic compound (cyano)(3-phenoxyphenyl)methyl (cis)-3-(2,2-dichloroethenyl)-2,2-dimethylcyclopropanecarboxylate has 4 isomers, designated I through IV:

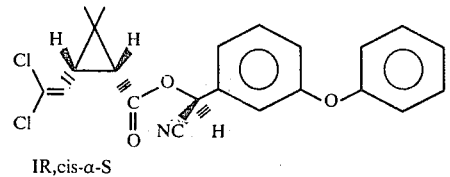

1R,cis-α-S

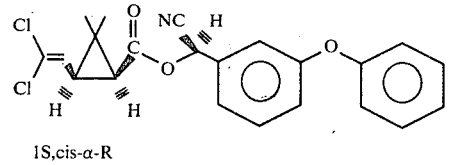

1S,cis-α-R

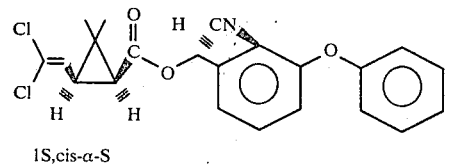

1S,cis-α-S

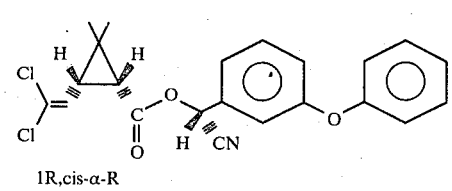

1R,cis-α-R

Throughout the specification the compound descriptions have been abbreviated as shown below structures I through IV. It will be understood that designations 1R,cis and/or 1S,cis refer to the spatial relationship of the hydrogen atoms at the 1 and 3 positions of the cyclopropane ring and the designations α-S and α-R refer to the spatial configuration of the cyano group on the α-carbon of the alcohol portion of the molecule. In this specification, omission of a limiting spatial designation indicates the compound is a racemic mixture of the possible isomers.

The U.S. patents cited above deal with an optically active pair of diastereomers of 1R,cis configuration corresponding to formulae I and IV above, mixtures of I and IV, or the corresponding dibromoethenyl analog. Preparation of these diastereomeric pairs can only be achieved by use of a cyclopropanecarboxylic acid which is resolved into the 1R,cis configuration. Commercially this is undesirable, as resolution is an expensive, time-consuming step, and results in loss of approximately one-half of the racemic starting material due to unavailability of a commercially acceptable means for epimerization at the 1 and 3 positions of the cyclopropane ring. The Japanese Kokai, on the other hand, utilized the mixture of all four isomers and recovered the "ineffective substances" as a crystalline material and the "effective substances" as an oil.

In accordance with the present invention, there is provided a crystalline, optically inactive compound in which each crystal contains substantially equimolar amounts of the isomers (S)-(cyano)(3-phenoxyphenyl)methyl (1R,cis)-3-(2,2-dichloroethenyl)-2,2-dimethylcyclopropanecarboxylate and (R)-(cyano)(3-phenoxyphenyl)methyl (1S,cis)-3-(2,2-dichloroethenyl)-2,2-dimethylcyclopropanecarboxylate. The compound of the present invention is a novel crystalline compound having unique physical properties differing significantly from those of the individual stereoisomers I and II or physical mixtures of I and II. For example each of the isomers I and II have a melting point in the range of 55° C. to 57° C., or lower depending on purity, whereas the claimed compound has a melting point considerably higher than either of the individual isomers. In a highly pure state the claimed compound has a melting point in the range of about 80° C. to about 83° C. This melting point is also considerably in excess of the melting point of the enantiomer pair containing isomers III and IV, approximately about 64° C. to about 66° C., or lower depending on purity. Of course, as the claimed compound is crystallized, it can be expected that a small amount of residual isomers III and IV will be adsorbed on the surface of the crystal or incorporated into the crystal itself, resulting in a lowering of the melting point for the claimed compound. Thus, a crystal of at least 90% purity with respect to isomers I and II may have a melting point in the range of about 72° C. to about 83° C., preferably in the range of 75° C. to about 83° C.

The claimed compound also has a unique crystal structure which distinguishes it over the individual isomers or mixtures thereof. The pure individual isomers produce slender, needlelike crystals and physical mixtures will also have that needle-like crystalline structure. The claimed compound, on the other hand, is a short, broad, rhomboidal crystal. Thus, the claimed compound is a true compound having properties not shared by the individual isomers contributing to its structure.

This invention also provides an insecticidal composition comprising an insecticidal amount of this compound in admixture with a compatible, agriculturally acceptable diluent, carrier or adjuvant, including mixtures thereof, and a cyclic crystallization process for producing the compound.

The process aspect of this invention is an improvement in cyclic process disclosed and claimed in prior application Ser. No. 046,147, a four step process requiring one solvent for a crystallization step and another for an equilibration step.

In accordance with the improved process claimed in this application, both the crystallization and equilibration steps may be conducted in a solvent of the type heretofore only used for crystallization. Both the four step process and the present process start with a mixture of the four isomers identified above (formulae I through IV), a racemic, substantially optically inactive mixture of the 1R,cis-α-S, 1S,cis-α-R, 1S,cis-α-S and 1R,cis-α-R isomers of (cyano)(3-phenoxyphenyl)methyl 3-(2,2-dichloroethenyl)-2,2-dimethylcyclopropanecarboxylate. In accordance with the process aspect of the present application, the need for a change of solvent between crystallization and equilibration steps has been eliminated by utilizing a first temperature for the crystallization step, then employing a higher second temperature for the equilibration step and continuously cycling the reaction mixture between these two temperatures. Thus the invention comprises (a) treating (R,S)-(cyano)(3-phenoxyphenyl)methyl (cis)-3-(2,2-dichloroethenyl)-2,2-dimethylcyclopropanecarboxylate with 1 to 10 cc per gram of an aliphatic or cycloaliphatic hydrocarbon of 5 to 8 carbon atoms at a first temperature below about 35° C. and separating from the resulting mixture the claimed compound and a mother liquor rich in the residual 1S,cis-α-S and 1R,cis-α-R isomers of (cyano)(3-phenoxyphenyl)methyl 3-(2,2-dichloroethenyl)-2,2-dimethylcyclopropanecarboxylate; then (b) heating said mother liquor to a second temperature of at least 40° C., up to reflux temperature of the solvent, in the presence of a base, preferably a strong base, for example, a lower alkyl, primary, secondary or tertiary amine, an alkali metal hydroxide or carbonate, titanium (IV) isopropoxide, 1,4-diazobicyclo[2.2.2]octane, or pyridine, to provide a solution of racemic (cyano)(3-phenoxyphenyl)methyl (cis)-3-(2,2-dichloroethenyl)-2,2-dimethylcyclopropanecarboxylate in which the ratio of the 1R,cis-α-S and 1S,cis-α-R isomers to the 1S,cis-α-S and 1R,cis-α-R isomers is from about 0.8:1 to about 1:1, the returning this solution to step (a).

In the crystallization step of the process racemic compound containing about 40% to 50% of the desired 1S,cis-α-R and 1R,cis-α-S isomers is treated with a non-polar solvent selected from the group consisting of an aliphatic or cycloaliphatic hydrocarbon of 5 to 8 carbon atoms to produce an optically inactive crystalline precipitate comprising substantially equimolar amounts of the 1R,cis-α-S, and 1S,cis-α-R isomers of (cyano)(3-phenoxyphenyl)methyl 3-(2,2-dichloroethenyl)-2,2-dimethylcyclopropanecarboxylic, and a mother liquor depleted of those isomers, but rich in the residual 1R,cis-α-R and 1S,cis-α-S isomers.

About 1 to 10 cc of solvent may be employed per gram of starting material, preferably about 2 to 5 cc/g, optionally 2 to 4 cc/g when the reaction is conducted at normal room temperature of 20°-25° C. The crystallization may, however, be conducted at a wide range of temperatures, for example in the range of −20° C. to about 35° C. Nucleation being shortly after the temperature is reduced from the equilibration temperature (of step (b), above) to below about 35° and is promoted by stirring or other means of agitation. Crystallization is generally allowed to proceed over a period of 3 to about 64 hours, but is suitably complete in 4 to 24 hours, at which time the crystalline product is separated from the mother liquor by any suitable means, for example, filtration.

The residual 1R,cis-α-R and 1S,cis-α-S isomers are then heated in the solvent used in the crystallization step, in the presence of a base, at a second temperature of at least 40° C., at which temperature equilibration begins to take place. The upper limit of this temperature is not known and may be up to the reflux temperature of the reaction mixture, perhaps higher if one chooses to operate under pressure.

In this step of the reaction, in which equilibration of the cyano group on the E-carbon takes place, temperature is a critical parameter, since equilibration takes place too slowly for practical application below about 40° C. The amount of base present, however, may vary over a wide range, for example from about 0.01 to 1 mole per mole of residual isomers (1S,cis-α-S and 1S,cis-αR) present in the mother liquor from step 1. However, since the amount of base does influence reaction rate, the presence of at least 0.1 to about 0.4 mole per mole is advantageously employed to avoid unecessarily extended reaction times. Suitable reaction times are generally in the range of about 4 to 24 hours, preferably 6 to about 18 hours. The solvent employed in this step is the same as that employed for the crystallization step. Additional solvent or base, to replace that lost in previous steps, may be added at anytime during or preceding this step, preferably after the crystallization step.

During this step heating is continued with agitation until epimerization about the α-carbon of the alcohol portion of the molecule has been completed or has substantially slowed, determined by high pressure liquid chromatography (hplc) of samples taken during the course of the reaction. Upon completion of this step, the temperature is lowered, additional starting material added to replace starting material previously removed by crystallization, and the crystallization step repeated.

The examples which follow, examples I through II demonstrate preparation of the compound of the invention in accordance with the 4 step process of U.S. Ser. No. 046,147, and examples III and IV demonstrate the preparation by the improved process.

EXAMPLE I

Synthesis of (cyano)(3-phenoxyphenyl)methyl (cis)-3-(2,2-dichloroethenyl)-2,2-dimethylcyclopropanecarboxylate A. Synthesis of (cyano)(3-phenoxyphenyl)methanol as an intermediate Into a flask were placed 755.7 g (2.5 moles) of the sodium salt of (hydroxy)(3-phenoxyphenyl)methanesulfonic acid, 237.6 g (1.25 moles) of sodium metabisulfite, and 2273 ml of water. The flask was cooled to 15° C. and a solution of 245.1 g (5.0 moles) of sodium cyanide in 302 ml of water was added dropwise. The reaction mixture was allowed to warm to room temperature, was stirred for 3 hours, then extracted three times with 800 ml of diethyl ether. The extract was washed once with 800 ml of a solution of 25% sodium metabisulfite and 1 N hydrochloric acid and twice with distilled water. After being dried over magnesium sulfate, the ether was evaporated, leaving a residue of 498.5 g of 94% (cyano)(3-phenoxyphenyl)methanol by gc analysis.

B. Synthesis of (cis)-3-(2,2-dichloroethenyl)-2,2-dimethylcyclopropanecarboxylic acid chloride as an intermediate In a flask were placed 400 g (1.913 moles) of cis-3-(2,2-dichloroethenyl)-2,2-dimethylcyclopropanecarboxylic acid and sufficient thionyl chloride to create a slurry. The remainder of the thionyl chloride (total used was 412.6 g (5.74 moles)) was added dropwise with stirring under a nitrogen blanket, and the reaction mixture was stirred at room temperature overnight. The crude product was distilled at 66°–67° C. at 66.7 Pa (0.5 mm of Hg) to produce 426.4 g of 98% (cis)-3-(2,2-dichloroethenyl)-2,2-dimethylcyclopropanecarboxylic acid chloride.

C. Synthesis of (cyano)(3-phenoxyphenyl)-methyl (cis)-3-(2,2-dichloroethenyl)-2,2-dimethylcyclopropanecarboxylate A mixture of 468.6 g (2.08 moles) (cyano)(3-phenoxyphenyl)methanol and 2500 ml toluene was placed in a flask and heated to 40° C. During an 80–85 minute period, 509 g (2.24 moles) of (cis)-3-(2,2-dichloroethenyl)-2,2-dimethylcyclopropanecarbonyl chloride prepared as described in Step B, and 186 g (2.35 moles) of pyridine were added under nitrogen. Upon completion of the addition, the reaction mixture was stirred 2.5 hours at 40° C. After cooling, the reaction mixture was washed successively with 1000 ml of water, 1000 ml of 1 N hydrochloric acid, 1000 ml of 1 N sodium hydroxide, twice with water, and once with an aqueous solution of sodium chloride. After being dried over magnesium sulfate, the solution was filtered through Celite and the solvent stripped using a rotary evaporator. Residual solvent was removed in a vacuum oven. A total of 918.3 g of 93.6% (cyano)(3-phenoxyphenyl)-methyl cis-3-(2,2dichloroethenyl)-2,2-dimethylcyclopropanecarboxylate was obtained.

EXAMPLE II

Crystallization of a racemic mixture of (S)-(cyano)-(3-phenoxyphenyl)methyl (1R,cis)-3-(2,2-dichloroethenyl)-2,2-dimethylcyclopropanecarboxylate and (R)-(cyano)(3-phenoxyphenyl)methyl (1S,cis)-3-(2,2-dichloroethenyl)-2,2-dimethylcyclopropanecarboxylate and base catalyzed diestereomeric equilibration of the residue Four samples of the product of Example 1.C., weighing 193.4 g, 182.9 g, 249.2 g, and 284.5 g, were dissolved in hexane, the first two in 550 ml of hexane, the third in 700 ml of hexane, and the fourth in 750 ml of hexane. After stirring overnight the precipitate was filtered off. From the first two samples a total of 96 g was isolated and from the third and fourth portions a total of 132 g was isolated. The combined solids were washed with 576 ml of hexane, giving 212.9 g of solid which had a melting point of 79°–81° C. Analysis by nmr confirmed that this solid was a racemic mixture of (S)-(cyano)(3-phenoxyphenyl)methyl (1R,cis)-3-(2,2-dichloroethenyl)-2,2-dimethylcyclopropanecarboxylate and (R)-(cyano)(3-phenoxyphenyl)methyl (1S,cis)-3-(2,2-dichloroethenyl)-2,2-dimethylcyclopropanecarboxylate. An additional 9.60 g of solid was recovered from the combined filtrates from the first and second samples after a second period of stirring. All filtrates and washings were combined and stripped of hexane using a rotary evaporator. The yellow, viscous oil that was recovered weighed 658.9 g. This oil was placed in a flask, and 1650 ml of toluene and 82 ml of triethylamine were added to the flask. After stirring for over 40 hours, the mixture was washed successively with 800 ml of 1 N hydrochloric acid, 800 ml of 1 N sodium hydroxide, once with water, and twice with a saturated aqueous solution of sodium chloride. The solution was dried over magnesium sulfate and then filtered through Celite. Removal of the toluene using a rotary evaporator left an amber, viscous oil weighing 648.9 g. Analysis by nmr showed that treatment with triethylamine has restored the ratio of isomers to that found in the product of Example I.C.

EXAMPLE III

Crystallization-equilibration of (R,S)-(cyano)(3-phenoxyphenyl)methyl cis-3-(2,2-dichloroethenyl)-2,2-dimethylcyclopropanecarboxylate in hexane.

A. Crystallization of (R)-(cyano)(3-phenoxyphenyl)-methyl (1S-cis)-3-(2,2-dichloroethenyl)-2,2-dimethylcyclopropanecarboxylate and (S)-(cyano)(3-phenoxyphenyl)methyl (1R-cis)-3-(2,2-dichloroethenyl)-2,2-dimethylcyclopropanecarboxylate (R,S)-(cyano)-(3-phenoxyphenyl)methyl cis-3-(2,2-dichloroethenyl)-2,2-dimethylcyclopropanecarboxylate (236.9 g, containing 49% of the desired enantiomer pair by hplc analysis) was dissolved in hexane (1400 ml). The solution was equally divided into two portions and each portion was placed in a one liter resin flask and stirred for 5 hours at 31° C. The crystals formed were filtered and washed with cold hexane to yield 63.4 g of 91% product by hplc analysis, mp. 78°–81° C., containing equimolar amounts of the 1R,cis-α-S/1S,cis-α-R enantiomer pair of (cyano)-3-(phenoxyphenyl)methyl 3-(2,2-dichloroethenyl)-2,2-dimethylcyclopropanecarboxylate.

B. Equilibration of (R,S)-(cyano)(3-phenoxyphenyl)methyl cis-3-(2,2-dichloroethenyl)-2,2-dimethylcyclopropanecarboxylate in fresh hexane The filtrate from Step A was flash evaporated to give 173.5 g of a racemic (cyano)(3-phenoxyphenyl)methyl cis-3-(2,2-dichloroethenyl)-2,2-dimethylcyclopropanecarboxylate, containing 36%, by hplc, of the 1R,cis-α-S/1S,cis-α-R enantiomer pair. This mixture was dissolved in hexane (875 ml), and triethylamine (17 g) was added. The solution was stirred in a one liter flask for 20 hours at 40° C., following which hplc analysis showed 49% of that enantiomer pair. The temperature was then lowered to 31° C. for 5 hours, then filtered to provide 11.3 g of product containing equimolar amounts of the 1R,cis-α-S and 1S,cis-α-R enantiomer pair having a melting point of 79°–81° C. This cycle of crystallization-equilibration was repeated seven times. The eight samples accounted for 80% of the available (R,S)-(cyano)(3-phenoxyphenyl)methyl cis-3-(2,2-dichloroethenyl)-2,2-dimethylcyclopropanecarboxylate, crystallized as the desired product. Each sample had a melting point range of approximately 79°–81° C.

EXAMPLE IV

Stepwise crystallization-equilibration of (R,S)-(cyano)(3-phenoxyphenyl)methyl cis-3-(2,2-dichloroethenyl)-2,2-dimethylcyclopropanecarboxylate in hexane.

(R,S)-(cyano)(3-phenoxyphenyl)methyl cis-3-(2,2-dichloroethenyl)-2,2-dimethylcyclopropanecarboxylate (100 g, containing 43% of the desired enantiomer pair, by hplc), was dissolved in hexane (500 ml) containing triethylamine (10 g) and the solution was refluxed for one hour. The mixture was then transferred to a resin flask and stirred for seven hours at 45° C. The temperature was then adjusted to 31° C. and the mixture stirred for eighteen hours, and filtered; and the recovered crystals were washed with cold hexane. If the crystals were analyzed by hlpc as being <90% of the desired enantiomer pair, (S)-(cyano)(3-phenoxyphenyl)methyl 1R-cis-3-(2,2-dichloroethenyl)-2,2-dimethylcyclopropanecarboxylate and (R)-(cyano)(3-phenoxyphenyl)methyl 1S-cis-3-(2,2-dichloroethenyl)-2,2-dimethylcyclopropanecarboxylate, they were recombined with the mother liquor. If the crystals were >90% of the desired enantiomer pair, they were set aside and their weight was replaced with (R,S)-(cyano)(3-phenoxyphenyl)methyl cis-3-(2,2-dichloroethenyl)-2,2-dimethylcyclopropanecarboxylate, from the original feedstock. Additional triethylamine was added to maintain a 10% weight ratio to the racemic mixture, as determined by gc. This cycle was repeated seventeen times and a total of 172 g of the desired compound crystallized from 255 g of the racemic mixture. The recovered crystals contained from 89 to 97 percent, by hplc, of the desired enantiomer pair.

The compounds prepared in accordance with the method aspect of this invention are applied to the locus where insect control is desired, for example, to the insect itself or to the foliage or seeds of agricultural plants. The compounds are useful for the control of household, veterinary, and crop insects and may be applied as technical material or as a formulated product. Typical formulations include compositions of the active ingredient in combination with an agriculturally acceptable carrier or extender, optionally with an adjuvant such as a surface-active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of the active ingredient depending upon the particular agent used, the additives and carriers used, other active ingredients, and the desired mode of application. With due consideration of these factors, the active ingredient of a typical formulation may, for example, be suitably present at a concentration of about 0.1% up to about 95% by weight of the formulation. An agriculturally acceptable carrier or extender may comprise about 99.9% by weight to as low as about 5.0% by weight of the formulation. Compatible surface-active agents, if employed in the formulation, may be present at various concentrations, suitably in the range of 1% to 30% by weight of the formulation.

The formulation may be used as such or diluted to a desired use dilution with a diluent or carrier suitable for facilitating dispersion of the active ingredients. The concentration of the active ingredient in the use dilution may be in the range of about 0.01 to about 10% by weight. Many variations of spraying, dusting, and controlled or slow release compositions of a type known in the art may be used by substituting or adding a compound of this invention into the compositions known or apparent to the art.

The compounds of this invention may be formulated and applied with other compatible active agents, including nematicides, insecticides, acaricides, fungicides, plant regulators, herbicides, fertilizers, synergists such as piperonyl butoxide, or a combination of these.

In applying these compounds, whether alone or with other agricultural chemicals, an effective insecticidal amount of the active ingredient must be applied. While the application rate will vary widely depending on the choice of compound, the formulation, mode of application, the plant species being protected, and the planting density, a suitable use rate may be in the range of 0.005 to 3 kg./hectare, preferably 0.01 to about 1 kg./hectare.

The compounds of this invention were tested for initial insecticidal activity as described below.

EXAMPLE V

Topical Application Test:

The compound of this invention was tested for insecticidal activity by applying to the insect appropriate amounts of a toxicant solution containing 5 mg/ml of toxicant in acetone. The tests were read twenty-four hours after application of the toxicant solution and the percent kill determined. The commercial insecticide permethrin, 3-phenoxybenzyl (+) cis-trans-3-(2,2-dichlorovinyl)-2,2-dimethylcyclopropanecarboxylate, was used as the standard for comparison. Relative potency, based on a value of 1.0 for permethrin, was determined by comparing the $LD_{50}$ for the test compound with that for the standard. The insects employed include southern armyworm (*Spodoptera eridania* [Cram.]), cabbage looper (*Trichoplusia ni* [Hubner]), Mexican bean beetle (*Epilachna varivestis* Muls.), beet armyworm (*Spodoptera exigua* [Hubner]), milkweed bug (*Oncopeltus faciatus* [Dallas]), tobacco budworm (*Heliothis virescens* [Fabricius]), and corn earworm (*Heliothis zea* [Boddie]). The results of these tests are shown in the table below. Except for southern armyworm, the compound of the invention was several times as active as permethrin.

| Topical Application Test | | | | | | | |
|---|---|---|---|---|---|---|---|
| | Insects[a] | | | | | | |
| | BAW | CEW | CL | MBB | MWB | SAW | TBW |
| $LD_{50}$[b] | 218.8 | 110.9 | 14.9 | 2.03 | 16.4 | 12.9–21.2 | 130.6–172.6 |
| Relative Potency | 5.1 | 2.5 | 9.0 | 7.2 | 37.6 | 1.0–1.5 | 4.2–6.1 |

[a]BAW = beet armyworm (*Spodoptera exigua*)
CEW = corn earworm (*Heliothis zea*)
CL = cabbage looper (*Trichoplusia ni*)
MBB = Mexican bean beetle (*Epilachna varivestis*)
MWB = milkweed bug (*Oncopeltus fasciatus*)
SAW = southern armyworm (*Spodoptera eridania*)
TBW = tobacco budworm (*Heliothis virescens*)
[b]ng/insect

EXAMPLE VI

Initial Contact (Foliar) Activity:

The compound of the invention was dissolved in a solution of 90% water, 9.75% acetone; and 0.25% octylphenoxypolyethoxyethanol to give a solution having 512 ppm (w/w) active ingredient. Aliquots of this solution were diluted with an appropriate amount of water to provide solutions containing various concentrations of active ingredient. Test organisms and techniques were as follows: The activity against Mexican bean beetle (*Epilachna varivestis Muls.*) and southern armyworm (*Spodoptera eridania* [Cram.]) was evaluated by spraying the leaves of pinto bean plants with the test solution and infesting with 3rd instar larvae after the foliage had dried. The activity against the pea aphid (*Acyrthosiphon pisum* [Harris]) was evaluated on broad bean plants whose leaves were sprayed before infestation with adult aphids. To prevent escape of the insects from the test site, the complete test plant or the incised leaves were placed in capped paper cups. The tests were transferred to a holding room for an exposure period of 48 hours. At the end of this time the dead and living insects were counted, the $LD_{50}$ was calculated, and the potency relative to the commercial insecticide permethrin, 3-phenoxybenzyl (+) cis,trans-3-(2,2-dichloroethenyl)-2,2-dimethylcyclopropanecarboxylate determined. The $LC_{50}$ and relative potency are reported in the table below. The foliar activity of the compound of the invention was several times greater than that for permethrin on pea aphid and southern armyworm as well as Mexican bean beetle.

| Initial Contact (Foliar) Activity | | | |
|---|---|---|---|
| | Insects[a] | | |
| | MBB | PA | SAW |
| $LC_{50}$[b] | 1.62–1.86 | 1.39–21.15 | .22–.38 |
| Relative Potency | 5.3–8.8 | 2.5–9.8 | 9.8–16.1 |

[a]MBB = Mexican bean beetle (*Epilachna varivestis*)
PA = pea aphid (*Acyrthosiphon pisum*)
SAW = southern armyworm (*Spodoptera eridania*)
[b]concentration in parts per million

I claim:

1. A crystalline insecticidal compound, each crystal of which comprises substantially equimolar amounts of the isomers of the enantiomer pair (S)-(cyano)(3-phenoxyphenyl)methyl (1R,cis)-3-(2,2-dichloroethenyl)-2,2-dimethylcyclopropanecarboxylate and (R)-cyano)(3-phenoxyphenyl)methyl (1S-cis)-3-(2,2-dichloroethenyl)-2,2-dimethylcyclopropanecarboxylate.

2. The compound of claim 1 in which the melting point is in the range of 72° C. to 83° C.

3. An insecticidal composition comprising the compound of claim 1 or 2 in admixture with an agriculturally acceptable adjuvant, diluent or carrier.

4. A method for control of insects in agricultural crops which comprises applying to the locus of infestation an insecticidally effective amount of the composition of claim 3.

* * * * *

UNITED STATES PATENT AND TRADEMARK OFFICE
CERTIFICATE OF CORRECTION

PATENT NO. : 4,308,279
DATED : December 29, 1981
INVENTOR(S) : Leland A. Smeltz

It is certified that error appears in the above—identified patent and that said Letters Patent is hereby corrected as shown below:

Column 1, line 30, "diasterometer" should read --diastereomer--. Column 4, line 14, "the" should read --and--; line 21, "prefcipitate" should read --precipitate--; line 24, "thenyl)-2,2-dimethylcyclopropanecarboxylic," should read --thenyl)-2,2-dimethylcyclopropanecarboxylate,--; line 52, "E-carbon" should read --α-carbon--. Column 8, line 61, "(+)" should read --(±)--. Column 10, line 7, "(+)" should read --(±)--.

Signed and Sealed this

Twelfth Day of March 1985

[SEAL]

Attest:

DONALD J. QUIGG

Attesting Officer

Acting Commissioner of Patents and Trademarks